United States Patent
Wihl et al.

[11] Patent Number: 6,052,478
[45] Date of Patent: *Apr. 18, 2000

[54] AUTOMATED PHOTOMASK INSPECTION APPARATUS

[75] Inventors: Mark Joseph Wihl, Tracy; Tao-Yi Fu, Fremont; Marek Zywno, San Jose, all of Calif.; Damon Floyd Kvamme, Ann Arbor, Mich.; Michael E. Fein, Mountain View, Calif.

[73] Assignee: KLA-Tencor Corporation, San Jose, Calif.

[*] Notice: This patent is subject to a terminal disclaimer.

[21] Appl. No.: 08/727,985

[22] Filed: Oct. 9, 1996

Related U.S. Application Data

[63] Continuation of application No. 08/202,868, Feb. 25, 1994, Pat. No. 5,572,598, which is a continuation of application No. 07/748,984, Aug. 22, 1991, abandoned.

[51] Int. Cl.[7] .................................................. G06K 9/00
[52] U.S. Cl. .......................................... 382/144; 382/149
[58] Field of Search .................................. 382/141, 144, 382/145, 148, 149; 364/468.28, 478.08; 348/126, 129; 356/394, 398

[56] References Cited

U.S. PATENT DOCUMENTS

| | | | |
|---|---|---|---|
| 3,851,951 | 12/1974 | Eveleth | 350/161 |
| 4,247,203 | 1/1981 | Levy et al. | 356/398 |
| 4,500,202 | 2/1985 | Smyth | 356/237 |
| 4,549,206 | 10/1985 | Suzuki et al. | 358/106 |
| 4,579,455 | 4/1986 | Levy et al. | 356/394 |
| 4,633,504 | 12/1986 | Wihl | 382/54 |
| 4,644,172 | 2/1987 | Sandland et al. | 250/548 |
| 4,669,885 | 6/1987 | Ina | 356/443 |
| 4,778,984 | 10/1988 | Nakamura | 250/201 |
| 4,805,123 | 2/1989 | Specht et al. | 364/559 |
| 4,908,871 | 3/1990 | Hara et al. | 382/8 |
| 4,910,690 | 3/1990 | Fujita | 364/561 |
| 4,916,340 | 4/1990 | Negishi | 310/12 |
| 4,926,081 | 5/1990 | Yamamoto et al. | 256/354 |
| 4,926,489 | 5/1990 | Danielson et al. | 382/8 |
| 4,969,200 | 11/1990 | Manns et al. | 382/288 |
| 5,008,851 | 4/1991 | Brandstetter et al. | 364/807 |
| 5,048,967 | 9/1991 | Suzuki et al. | 356/401 |
| 5,098,191 | 3/1992 | Noguchi et al. | 356/394 |
| 5,133,601 | 7/1992 | Cohen et al. | 356/359 |
| 5,231,621 | 7/1993 | Matsui et al. | 369/44.32 |
| 5,311,598 | 5/1994 | Bose et al. | 382/8 |
| 5,572,598 | 11/1996 | Wihl et al. | 382/144 |

Primary Examiner—Yon J. Couso
Attorney, Agent, or Firm—Carr & Ferrell LLP

[57] ABSTRACT

An automated photomask inspection apparatus including an XY state (12) for transporting a substrate (14) under test in a serpentine path in an XY plane, an optical system (16) comprising a laser (30), a transmission light detector (34), a reflected light detector (36), optical elements defining reference beam paths and illuminating beam paths between the laser, the substrate and the detectors and an acousto-optical beam scanner (40, 42) for reciprocatingly scanning the illuminating and reference beams relative to the substrate surface, and an electronic control, analysis and display system for controlling the operation of the stage and optical system and for interpreting and storing the signals output by the detectors. The apparatus can operate in a die-to-die comparison mode or a die-to-database mode.

46 Claims, 7 Drawing Sheets

AUTOMATED PHOTOMASK INSPECTION APPARATUS

This application is a continuation of Ser. No. 08/202,868, filed Feb. 25, 1994, now U.S. Pat. No. 5,572,598, which is a continuation of Ser. No. 07/748,984 filed Aug. 22, 1991 abandoned.

BACKGROUND OF THE INVENTION

1. Field of the Invention

The present invention relates generally to electro-optical inspection systems, and more particularly to an automated photomask inspection apparatus for detecting defects on optical masks and reticles and the like.

2. Brief Description of the Prior Art

Integrated circuits are made by photolithographic processes which use photomasks or reticles and an associated light source to project a circuit image onto a silicon wafer. A high production yield is contingent on having defectless masks and reticles. Since it is inevitable that defects will occur in the mask, these defects have to be found and repaired prior to using the mask.

Automated mask inspection systems have existed for over 15 years. The earliest such system, the Bell Telephone Laboratories AMIS system (John Bruning et al., "An Automated Mask Inspection System—AMIS", *IEEE Transactions on Electron Devices*, Vol. ED-22, No. 7 July 1971, pp 487 to 495), used a laser that scanned the mask. Subsequent systems used a linear sensor to inspect an image projected by the mask, such as described by Levy et al. (U.S. Pat. No. 4,247,203, "Automatic Photomask Inspection System and Apparatus") who teach die-to-die inspection, i.e., inspection of two adjacent dice by comparing them to each other. Alternately, Danielson et al. (U.S. Pat. No. 4,926,489, "Reticle Inspection System") teach die-to-database inspection, i.e. inspection of the reticle by comparison to the database from which the reticle was made.

As the complexity of the integrated circuits has increased, so has the demand on the inspection process. Both the need for resolving smaller defects and for inspecting larger areas have resulted in much greater speed requirements, in terms of number of picture elements per second processed. The increased demands have given rise to improvements described in a number of subsequently issued patents, such as U.S. Pat. Nos. 4,247,203, entitled "Automatic Photomask Inspection System and Apparatus", Levy et al., issued Jan. 27, 1981; 4,579,455, entitled "Photomask Inspection Apparatus and Method with Improved Defect Detection", Levy et al., issued Apr. 1, 1986; 4,633,504, entitled "Automatic Photomask Inspection System Having Image Enhancement Means", Mark J. Wihl, issued Dec. 30, 1986; and 4,805,123, entitled "Automatic Photomask Inspection and Reticle Inspection Method and Apparatus Including Improved Defect Detector and Alignment Subsystem", Specht et al., issued Feb. 14, 1989. Also of relevance is some prior art in the wafer inspection area, such as U.S. Pat. No. 4,644,172, entitled "Electronic Control of an Automatic Wafer Inspection System", Sandland et al., issued Feb. 17, 1987.

Another force driving the development of improved inspection techniques is the emergence of phase shift mask technology. With this technology it will be possible to print finer linewidths, down to 0.25 micrometers or less. This technology is described by Burn J. Lin, "Phase-Shifting and Other Challenges in Optical Mask Technology", *Proceedings of the 10th Annual Symposium on Microlithography. SPIE*,—the International Society of Optical Engineering, Vol. 1496, pages 54 to 79.

The above improvements teach the automatic detection of defects on conventional optical masks and reticles. In all of these systems, conventional lighting is used and the images are captured by linear array sensors. These two system choices limit the signal-to-noise ratio and hence the speed of inspection.

SUMMARY OF THE INVENTION

An important object of present invention is to provide a novel defect detection apparatus which can use both transmitted and reflected light to inspect a substrate.

Another object of the present invention to provide a device of the type described in which surface elevations above a reference elevation are optically determined using interferrometric principals and used as indicators of defects.

Another object of the present invention is to provide a device of the type described which uses the same optical system to detect defects and measure line widths.

Briefly, a preferred embodiment of the present invention includes an XY state (12) for transporting a substrate (14) under test in a serpentine path in an XY plane, an optical system (16) comprising a laser (30), a transmission light detector (34), a reflected light detector (36), optical elements defining reference beam paths and illuminating beam paths between the laser, the substrate and the detectors and an acousto-optical beam scanner (40, 42) for reciprocatingly scanning the illuminating and reference beams relative to the substrate surface, and an electronic control, analysis and display system for controlling the operation of the stage and optical system and for interpreting and storing the signals output by the detectors. The apparatus can operate in a die-to-die comparison mode or a die-to-database mode.

One advantage of the present invention is that it uses a laser light source and hence has a much higher brightness to scan the mask. It differs from the AMIS system described by Bruning et al. in that it employs an electro-optical deflection method instead of a mechanical system. Obviously the electro-optical method is faster and more flexible than a mechanical device. However, even conventional electro-optical deflections do not have sufficient speed to meet system requirements. In the present invention the speed is further enhanced by the use of a deflection apparatus previously described for laser beam recording by U.S. Pat. No. 3,851,951 to Jason H. Eveleth, entitled "High Resolution Laser Beam Recorder with Self-Focusing Acousto-Optic Scanner", issued Dec. 3, 1974.

Another advantage is the use of a stage that has only two degrees of freedom. Prior art also incorporated a rotational capability at a considerable cost and complexity. In the present invention the effective direction of scanning is controlled by driving both axes of the stage simultaneously.

Another significant departure from previous art is the ability of the present system to simultaneously detect defects with both transmitted and reflected light. This capability is significant because the additional information can be helpful in determining the nature of the defect and thereby permits the automatic classification of defects.

Yet another advantage of the present invention is its ability to inspect phase shift masks. It is anticipated that phase shift mask technology will be used in the 1990's to achieve linewidths of 0.10 micrometers. In the present invention the phase shift material can be measured at all points on a mask area at the normal scanning speed of the system.

Also advantageous is the ability of the present system to perform linewidth measurement on the mask. This is a significant advantage because heretofore two different types of instruments were employed to do both defect detection and linewidth measurement. The ability to use a single instrument results in a saving of time and, possibly more important, in less handling of the mask, which in turn is significant in contamination control.

A novel feature of the present invention is the autofocusing method employed. Previous mask inspection systems used autofocus systems that were affected by the pattern on the mask. The present invention functions independently of the pattern.

A significant innovation of the present system is also the two-axis preloading of the stage air bearings. Exceptional stiffness is achieved by this angular loading method.

Also new is the method of correcting for variations of light intensity. In the prior art the spatial non-uniformity of the illumination was determined before an inspection but no provisions existed for compensating for changing non-uniformity during inspection or, more likely, variations of the absolute level of intensity during the inspection. In the present invention the intensity is constantly monitored and immediately compensated in real time. Hence, variations of the primary light source with time do not affect the accuracy of the inspection process.

Yet another new capability of the present invention is to inspect the mask at substantially the same wave length as used for wafer printing (exposure) through the mask. With advances in technology, increasingly shorter wavelengths are used for printing. Because the appearance of defects changes depending on the wavelength of the illumination, it is important to employ approximately the same wavelength light source for both inspection and printing.

These and other objects and advantages of the present invention will no doubt become apparent to those skilled in the art after having read the following detailed disclosure of the preferred embodiments illustrated in the several figures of the drawing.

IN THE DRAWING

DETAILED DESCRIPTION OF THE PREFERRED EMBODIMENTS

Figure 1:
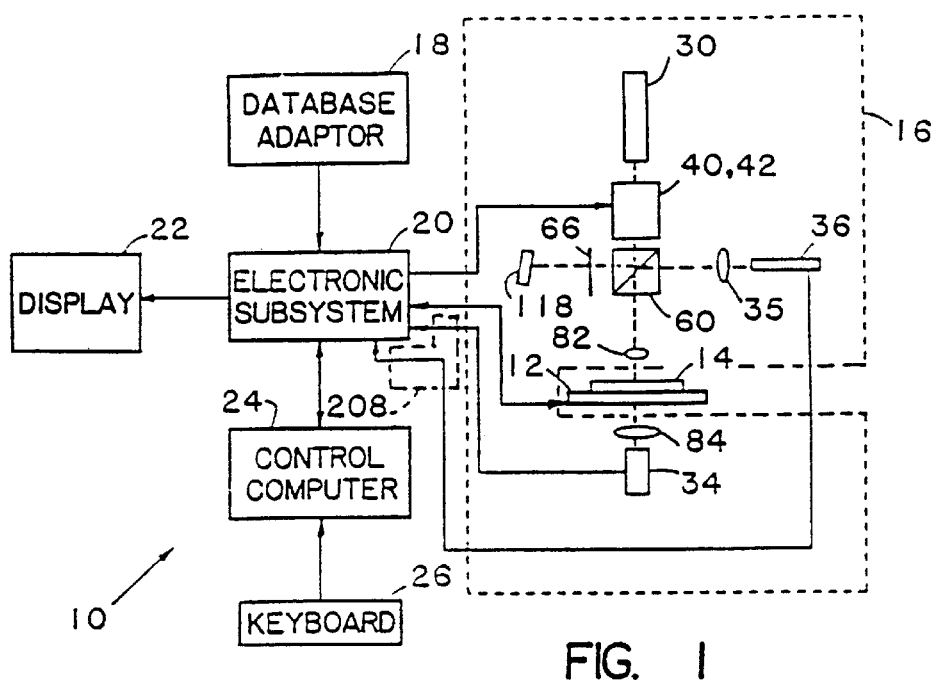
FIG. 1 is a simplified functional block diagram of a laser mask inspection system in accordance with the present invention.

Referring now to FIG. 1, a block diagram of an automatic optical inspection system in accordance with the present invention is shown at 10. The system is capable of inspecting substrates, such as reticles, photomasks, semiconductor wafers and phase shift masks.

The system can perform several types of inspection: transmitted light inspection, reflected light inspection, simultaneous reflected and transmitted inspection, and phase shift measurement. In transmitted light inspection, light impinges on the substrate, a photomask for example, and the amount of light transmitted through the mask is detected. In reflected light inspection, the light reflecting from a surface of the substrate under test is measured. During phase shift inspection, the amount of phase shift between two reflected coherent light beams is detected at each point on the mask while transmitted light inspection takes place concurrently. The phase shift is proportional to the relative elevation of the surface from which the beams are reflected. As will be explained below, the transmitted light signal is used to qualify the phase-shift signal. In addition to these defect detection operations, the system is also capable of performing line width measurement.

In all of the defect detection operations a comparison is made between two images. In die-to-die inspection mode two areas of the substrate having identical features (dice) are compared with respect to each other and any substantial discrepancy is flagged as a defect. In the die-to-database inspection mode a defect is detected by comparing the die under test with corresponding graphics information obtained from the CADS (computer aided database system) database from which the die was derived. In the latter case the CADS database is converted to an image format as explained in U.S. Pat. No. 4,926,489. (Danielson at al., "Reticle Inspection System", issued May 15, 1990).

As depicted in the simplified block diagram of FIG. 1, a preferred embodiment of the system 10 is comprised of a stage 12 for carrying a substrate 14 to be inspected, an optical subsystem 16, a data base adaptor 18, an electronics subsystem 20, a display 22, a control computer 24 and a keyboard 26.

The Stage

Although a preferred embodiment of the stage 12 will be described in detail below, it suffices at this point to say that the stage is a precision device driver under control of subsystem 20 and capable of moving the substrate 12 under test in a serpentine fashion, within a single plane, relative to the optical axes of the optical subsystem 16 so that all or any selected part of the substrate surface may be inspected.

Optical Subsystem

Figure 2:
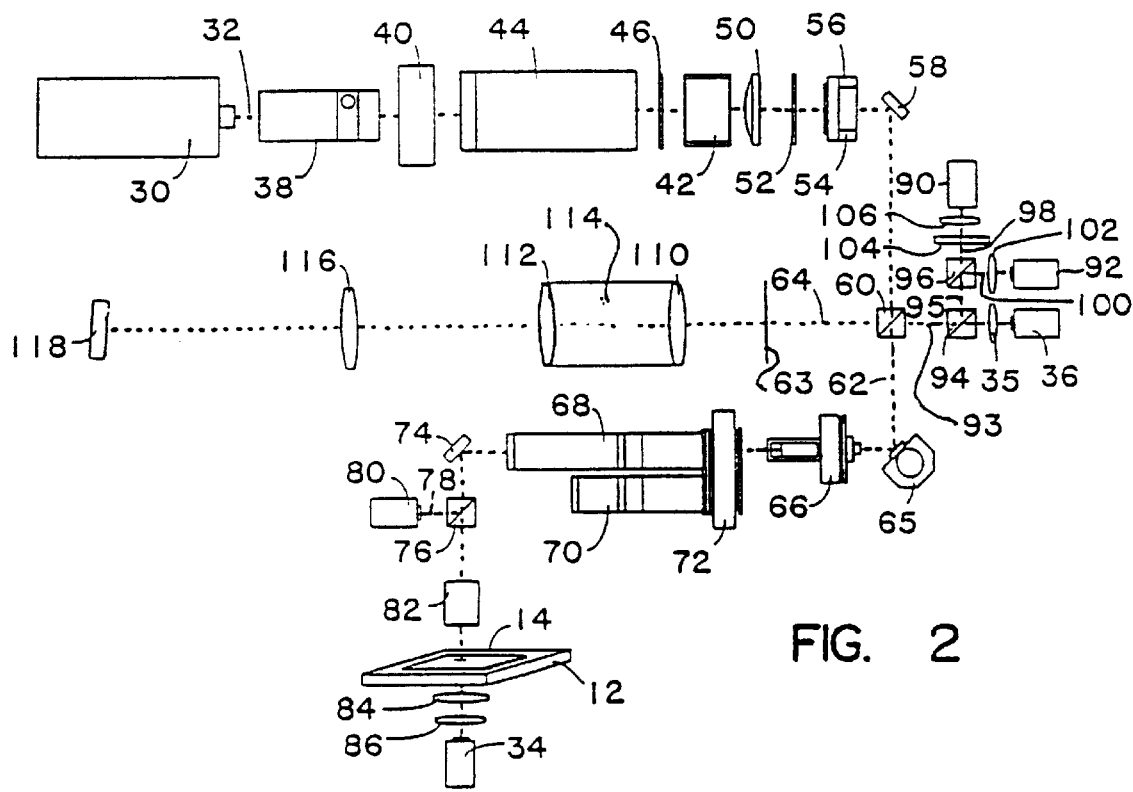
FIG. 2 is a more detailed schematic representation of the optical subsystem depicted in FIG. 1.
Figure 3:
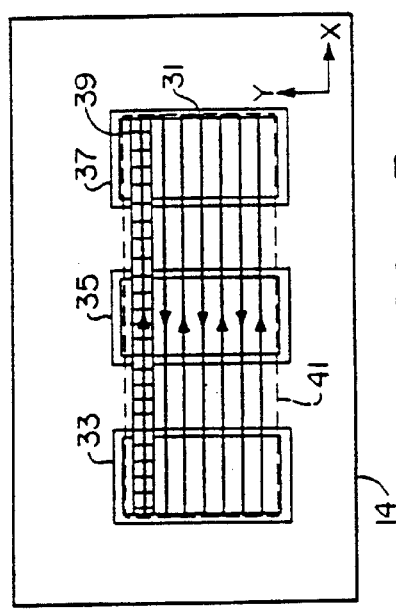
FIG. 3 is a diagram illustrating the scanning path used in the die-to-die inspection mode.
Figure 4:
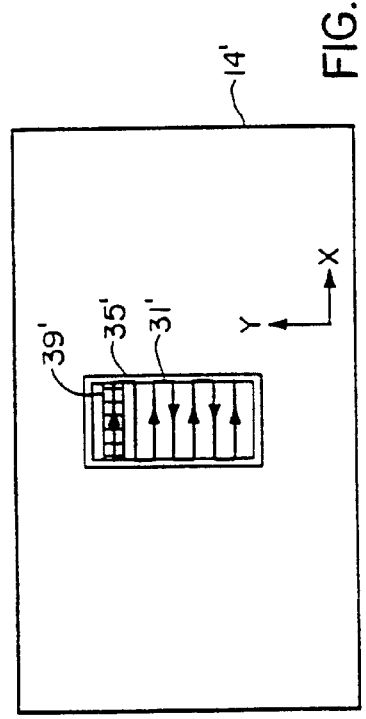
FIG. 4 is a diagram illustrating the scanning path used in die-to-database inspection mode.

A detailed block diagram of the optical subsystem 16 is shown in FIG. 2 and is essentially a laser scanner apparatus including a light source 30 and associated optics which cause a beam 32 of coherent light to be deflected back and forth over a small angle. As will be further described below, the beam sweep is in a direction such that, after passing through the optical system, it is directed parallel to the Y-axis as viewed at the substrate 14. As the beam is swept, the stage 12 carrying the substrate 14 under test is caused to move back and forth in the direction of the X-axis, being incremented in the Y-direction at the end of each traverse so that the beam 32 is caused to sweep along a serpentine path 31 across a plurality of identified substrate subareas 33, 35, 37 (individual dice in the case of a photomask) as indicated in FIGS. 3 and 4. In this manner the entire surface area of the substrate (mask) 14 is swept in a series of contiguous swaths 39 by the laser beam. In the case of a transparent or partially transparent substrate, detection of the image is accomplished by a transmission detector 34. In the case of a reflective or partially reflective substrate, the light reflected from the substrate is detected by a reflected light detector 36. As will be explained in more detail later, phase shift mask inspection is carried out by using both of these detectors simultaneously.

The light source 30 of the system is a laser, such as the Model 5490A5L-00C-115 made by Ion Laser Technology of Salt Lake City, Utah. The light beam 32, emitted by the laser 32, first passes through a spatial filter 38 and is then deflected by the combination two acousto optic elements; an acousto-optic prescanner 40 and an acousto-optic scanner 42. These two elements deflect the light beam in the Y-direction and focus it in the X-direction in a manner similar to that described in U.S. Pat. No. 3,851,951. (Jason H. Eveleth, "High Resolution Laser Beam Recorder with Self-focusing Acousto-optic Scanner", issued Dec. 3, 1974). The deflection system also includes a beam expander 44 and a quarter wave plate 46.

When the beam emerges from the scanner 42, it is convergent in the Y-direction, but collimated in the X-direction. A cylindrical lens 50 then also focuses the beam in the X-direction, with the focal plane for both X and Y axes lying at a field stop 52. The beam next passes through a quarter wave plate 54 and a relay lens 56.

The beam is then reflected by a mirror 58, the sole function of which is to fold the optical path. The redirected beam then enters a cube beam splitter 60 which divides it into paths 62 and 64. The latter path is used only in the phase measurement mode and is otherwise blocked by a shutter 63.

The beam continuing along path 62 is reflected by an oscillating mirror 65 which is held fixed during the inspection operation and is used only for displaying an image to an operator on an image display (not shown in FIG. 2) during alignment and review. A dove prism 66 is used to rotate the direction of the scan about the optical axis. The output of prism 66 is fed to one of the telescopes 68 and 70 mounted on a rotatable turret 72. The purpose of these telescopes is to vary the size of the scanning spot on the substrate 14 and thereby allow selection of the minimum detectable defect size. Since changing the magnification also varies the length of the scan, the swath width is also changed and therefore the inspection speed. (Only two telescopes are shown but obviously any number of telescopes, and therefore spot sizes, can be used.)

From the telescope the beam passes to a mirror 74 and then to a beam splitter 76 where the path is again split. The reflected portion of beam 78 is directed to a detector 80 which serves as a monitor of the beam intensity variation. The unreflected portion of the beam passes through an objective lens 82 which focuses the beam onto the substrate 14. Light passing through the substrate 14 is then collected by a condenser lens 84 and a collector lens 86, and focused onto the transmission detector 34.

Autofocus Subsystem

The autofocus function is based upon a monitoring of the shape of the light beam cross-section after it is passed through some anomorphic elements. The basic principal underlying the implementation is that a cylindrical lens produces astigmatism. In such a case a focussed beam first passes through best focus in one direction and then through best focus in the perpendicular direction. In between these two focal points along the beam path the beam cross section is oblong in one direction and transitions along the path through points where the beam cross section is circular and then oblong in a direction perpendicular to the previous direction. In this invention the optimum focus of the light impinging on the substrate is detected by monitoring the beam cross section of light reflected from the substrate 14. The shape of the beam cross section is monitored by two silicon quadrature photodiodes 90 and 92, such as made by Silicon Detector Corporation of Newbury Park, Calif.

As is explained in more detail below, the actual autofocus system consists of two optical paths which differ from each other in the direction of the astigmation. In one path the cylindrical lens has no curvature when viewed in the X-direction while in the other path, the cylindrical lens has no curvature in the Y-direction.

Figure 5:
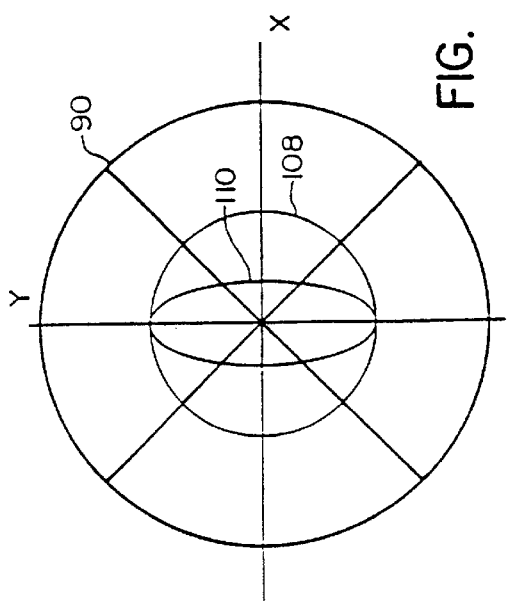
FIGS. 5 and 6 are diagrams illustrating possible beam cross sections used in the autofocus system.
Figure 6:
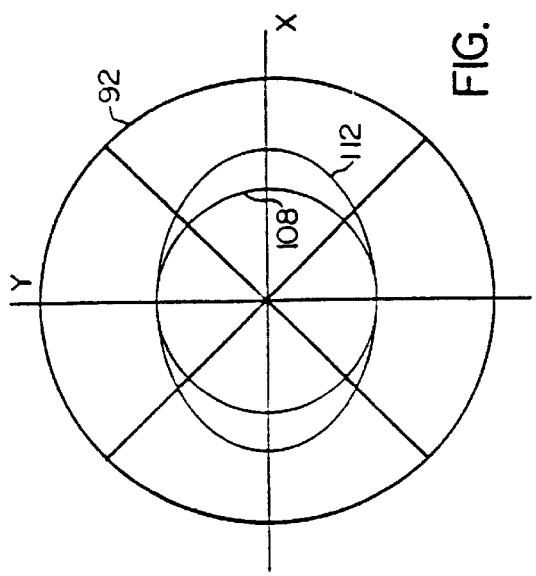

The autofocus beam 93 is split off from the reflected beam 95 directed along reflected detector path by a beam splitter 94, and is redirected toward another beam splitter 96 which splits the beam into two paths 98 and 100. In FIG. 2 the X-coordinate is perpendicular to the paper and consequently, cylindrical lens 102 is shown with a curvature, while an identical element 104, in the other path, appears as a plano-parallel element. The path leading to detector 90 also contains a spherical lens, 106. The two identical quadrature detectors 90 and 92 detect a cross-section of each beam. As the substrate surface position, or thickness, varies, the beam cross section, as seen by the detectors, varies in the X-direction as shown in FIGS. 5 and 6 at 108, 110 and 108, 112 respectively. It is to be noted that on neither detector does the vertical (Y-direction) diameter of the illuminated area change. When the mask is in focus, both detectors are illuminated by a circular beam 108. As the mask goes out of focus, the horizontal diameter shrinks on one detector (see FIG. 5), while on the other one it increases (see FIG. 6) as indicated by the outlines of the beam 110 and 112, respectively. This changes the electrical output from the quadrature detectors. The focus correction signal $F_c$ is then:

$$\frac{(A_1 - B_1) - (A_2 - B_2)}{(A_1 + B_1) + (A_2 + B_2)} \tag{1}$$

where $A_1$ is the signal derived from quadrants along the X axis of 90, $A_2$ is the signal derived from quadrants along the X axis of 92, $B_1$ is the signal derived from quadrants along the Y axis of 90, $B_2$ is the signal derived from quadrants along the Y axis of 92.

Transmitted Light Inspection Mode

Ordinarily, transmission mode detection is used for defect detection on substrates such as conventional optical masks having transparent areas and opaque areas. As the laser beam scans the mask, the light penetrates the mask at transparent points and is detected by transmitted light detector 34 which is located behind the mask 14 and measures the light collected by condenser lens 84 and collector lens 86.

Reflected Light Inspection Mode

Reflected light inspection is normally performed on opaque substrates that contain image information in the form of developed photoresist features. Light reflected by the substrate passes backwards along the same optical path as described before but is then diverted by a polarizing beam splitter 60 into detector 36. A condenser lens 35 projects the light onto the detector 36. As previously stated, during reflected light inspection, shutter 63 is closed.

Reflected light inspection may also be used to detect contamination on top of opaque substrate surfaces.

Phase Shift Material Thickness Measurement Mode

The measurement of phase shift is of interest only at points where the substrate is transparent, i.e., where there is no opaque geometry. The presence of opaque geometry is detected by the transmission detector 34 and only in the spaces separating such geometry is a phase shift measurement taken. During this operation shutter 63 is open and light from the laser reflected by splitter 60 travels through relay lenses 110 and 112, which form a telescope 114, and through a low numerical aperture objective lens 116 to a tilted mirror 118 where it is reflected back along the same path and through beam splitters 60 and 94, and condenser lens 35 to reflected light detector 36. At the same time, detector 36 is also illuminated by light which first passes through splitter 60 to be reflected from a point on the substrate and which on returning is reflected by splitter 60 to the detector. These two luminous beams interfere with each other, and the intensity of the light detected by detector 36 therefore varies as a function of the relative optical path length of the two paths 62 and 64. As will be explained in more detail later, this data is interpreted by the electronic subsystem to determine variations of thickness of phase shift material covering a given point on the substrate.

Simultaneous Detection by More than one Type of Detector

It is important to note that transmitted and reflected light inspections, and the phase shift measurement operation are not mutually exclusive in time. Simultaneous transmitted and reflected detection can disclose the existence of an opaque defect sensed by the transmitted detector while the output of the reflected detector can be used to disclose the type of defect. As an example, either a chrome dot or a particle is opaque and hence will result in a dark output from the transmission detector, but reflective chrome defects also produce a high reflected light indication while a particle will typically reflect less. By using both reflected and transmitted detection one may locate a particle on top of chrome geometry. In general, one may determine signatures for certain types of defects, such as the ratio of their reflected and transmitted light intensities. This information can then be used to automatically classify defects.

Similarly, transmitted light detection and phase shift measurement can occur simultaneously. On a phase shift mask an opaque defect in a region covered by phase-shift material can be detected, and the absence of opaque material detected by the transmitted light detector 34 can be used to gate the phase shift measurement.

Control Computer

The control computer, 24, acts as the operator console and master controller of the system and is a device such as a SPARC computer made by Sun Microsystems of Mountain View, Calif. All system interfaces with the operator and the user's facilities are made through the control computer. Commands are issued to and status is monitored from all other subsystems so as to facilitate completion of the operator assigned tasks.

Electronics Subsystem

The function of the electronics subsystem 20 is to interpret and execute the commands issued by control computer 24. These functions are: digitize the input from detectors 34 and 36; compensate these readings for variations in the incident light intensity; detect defects in the image and transfer the defect data to the control computer 24; accumulate the output of the interferometers used to track the stage 12; provide the drive for the stages linear motors; and monitor sensors which indicate status.

Except for the measurement of phase shift and line width information, all of the enumerated functions of control computer 24 and subsystem 20 have been described in the above-mentioned U.S. Pat. Nos. 4,247,203, 4,579,455, 4,633,504, 4,805,123, 4,926,489, and 4,644,172. It is to be noted that in the above patents the same functions are performed in many different ways and the particular approach adopted depended on the availability and suitability of integrated circuit devices at the time the system was being developed. Any of the cited approaches could be used.

The Stage

The stage 12 is an air-bearing X-Y stage that is driven by a linear motor on each axis. The position of the stage along each axis is monitored by interferometers (not shown), such as the Model TIPS V, made by Teletrac Corporation.

Figure 7:
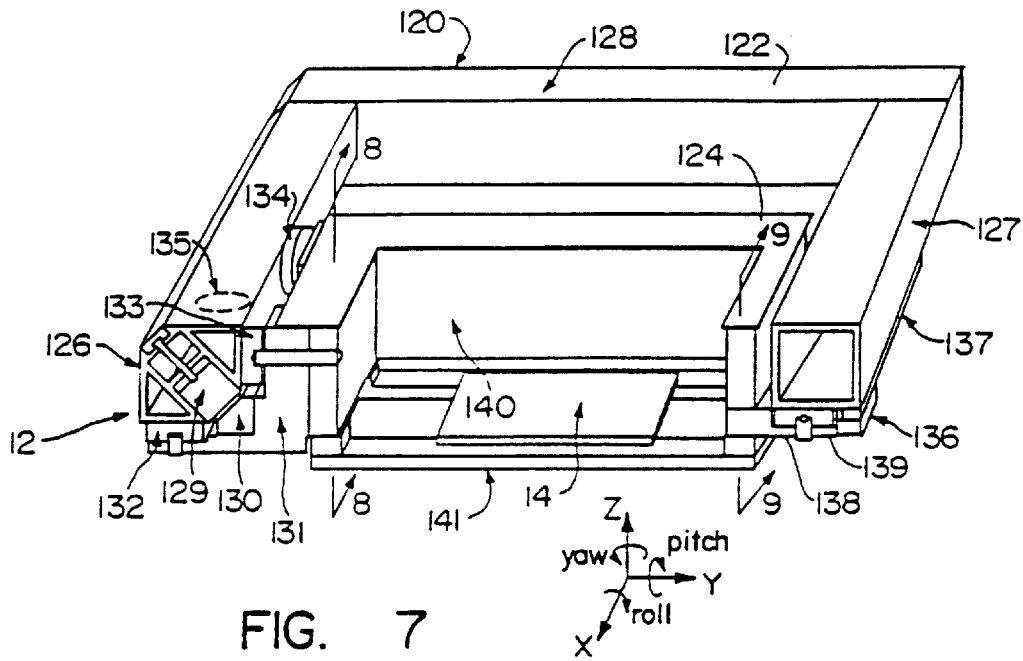
FIG. 7 is a partially broken perspective drawing illustrating the XY stage.

Stage 12 is shown in detail in FIG. 7 with the front rail cut away to permit view of the principal elements. The stage has two degrees of freedom; it has no rotational capability. It is disclosed here for application in the described inspection system but could also be used in microlithography and any precision machining application.

The Y carriage 120, in the shape of a frame 122, carries the X stage 124. The motion of both stages is controlled by linear motors and air bearings. The attractive force between the stator and the slider of each linear motor provides the preload of the linear bearings.

The Y carriage frame includes two guideways 126 and 127, controlling the motion of the X stage 124 inside the carriage. The guideways are connected by two side rails 128. (The front rail, the equivalent of 128, is not shown.) The stator 129 of the X linear motor is imbedded inside the X guideway 126 in such a way that it attracts the X slider 130 attached to air-bearing housings 131 and preloads four of the five X air bearings 132, 133, 134 and 135. A separate magnet 136 and ferromagnetic preload strip 137 provide the preload to air bearing 138. Each bearing is equipped with a swivel, enabling rotation of the bearing pad about two axes, in addition to rotating the bearing itself, thus the only degree of freedom constrained by an air bearing is the translation in the direction normal to the pad surface.

The X stage carries the substrate 14 and is kinematically constrained by the five air bearings: the bearings 132 and 135 control the pitch of the X stage motion, and constrain the vertical translation in the Z direction, bearings 133 and 134 control the yaw of the X motion and constrain the horizontal translation in the Y direction. Bearing 138 nested in the housing 139 controls the roll of the X stage and constrains vertical translation of the stage in the Z direction. The specimen holder assembly 140 is attached to a lightweight composite frame 141 of the X stage.

The stage contains a number of novel features. One such feature is the use the linear motor to preload the stage in two directions and thereby achieve an exceptional stiffness. This is accomplished by the arrangement of triangular cross section slider iron 130 and angular position of the stator 131, so that the magnetic attraction force is at an angle to all four air bearings 132, 133, 134 and 135.

Another innovative feature of the design is that the stator 129 of linear motor is imbedded inside the guideway 126 at an angle to the two walls of the guideway.

Figure 8:
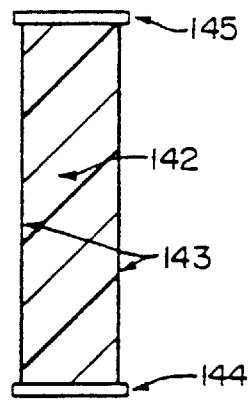
FIG. 8 is a cross-section taken along the line 8—8 of FIG. 7 showing details of the construction frame of the stage.

Also novel is the use of honeycomb material, such as Blue Seal, made by Hexcell of Dublin, Calif., for the construction of frame 140. This reduces the mass of the stage, yet makes it very rigid. A cross-section of this construction taken along the line 8—8 is shown in FIG. 8 where cellular insert 142 is sandwiched between skins 143. The bottom plate 144 and top plate 145 join the skins 143 and complete the box structure enclosing the insert 142. The honeycomb material may be replaced by any number of light composite materials, such as Duocell, manufactured by ERG of Oakland, Calif.

Figure 9:
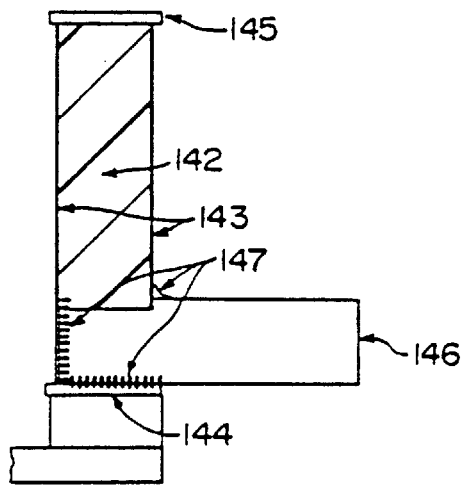
FIG. 9 is a cross-section taken along the line 9—9 of FIG. 7 showing other details of the construction frame of the stage.

Also novel is the method of attaching the solid pieces 146 to the composite in the way that they penetrate one skin of the composite wall and are attached to the opposite skin and either of the top or bottom plates, as shown in FIG. 9, with joints 147 formed around the penetration through the wall, and between the solid piece and the inside of the opposite skin and the plate 144.

OPERATION OF THE DISCLOSED EMBODIMENT

Alignment

Prior to starting the automatic inspection operation, the operator aligns the mask in the proper orientation and defines to the computer the "care area", i.e., the area to be inspected. FIG. 3 illustrates the desired orientation of the inspection path 31 with respect to dice 33, 35, and 37 shown here on a multi-die mask or reticle 14. During inspection, the stage 12 is moved in a serpentine manner, following the path 31, while the laser beam is deflected parallel to the Y-axis of the mask. As stage 12 moves in the X-direction, this Y-axis motion of the laser beam sweeps out a swath, 39. Ordinarily the axes of mask 14 will not be parallel to the drive axis of the stage. Therefore, an X or a Y directional motion of the stage requires both of the drives of the stage to be driven simultaneously. The first task of the operator is therefore to define to the system the ratio of the speeds of the major axes of the stage. To accomplish this, the operator chooses two points known to him to lie on the same X-coordinate of the die. He then drives the stage to these points, while observing the image on image display 22. The system notes the location of these points by measuring the travel with interferometers (not shown) along the drive axes of the stage. These measurements establish the direction cosines of the stage drive axes with respect to the X and Y axes of the mask. At this time the dove prism 66 (FIG. 2) is rotated to orient the deflection of the laser beam so that it is perpendicular to the X-directional travel of the stage. Next, the operator designates to the system the care area 41 (FIG. 3) of the die, the area to be inspected.

Phase Shift Measurement Calibration

For reasons that will become apparent later, in phase measurement mode, as the laser spot scans in the Y-direction, a flat transparent surface parallel to the plane of the mask, the intensity varies sinusoidally, as shown by curve 200 in FIG. 9. Mathematically, the intensity I is:

$$I = A \sin[(2\pi y/w) - D] + I_o \quad (2)$$

where y is the distance of the pixel in question from the origin, w is a constant that is a function of the tilt angle of mirror 118, D is the phase shift due to path length change as the result of the thickness of the phase shift material, A is the half-amplitude of the intensity, and $I_o$ is the intensity offset 204 due to stray light in the optics. These values are all determined during the phase shift measurement calibration part of the initialization. As the laser scans a flat uniform transparent area of the mask, the intensities at each picture element are digitized and stored in the computer. Then, $I_o$ is the average value of the intensities over integer cycles, and A can be computed from:

$$A = (I_{max} - I_o)/2 \quad (3)$$

The value W is the periodicity of the sinusoid.

It is to be noted that $I_o$ and A are different for clear and phase shift material covered areas and therefore must be determined for both areas. The quantity D is a linear function of the thickness of the phase shift material and this relationship is determined by calibration on a known sample containing various thickness phase shift material features and remains constant while the system retains dimensional stability.

The Inspection Process

Automatic inspection of a reticle ordinarily starts at the upper left hand corner of the care area and follows the serpentine pattern 31. As the stage slowly moves in the X direction, the laser beam rapidly sweeps back and forth in the Y-direction. In this manner a swath 39 is scanned and the digitized output of the detectors is stored in the electronics subsystem 20. When the swath reaches the left boundary of the care area of the second die 35, image data derived from die 33, and now stored in subsystem 20, is compared with the data derived from die 35. Any substantial difference is designated a defect. In a similar manner, the data from die 37 is also compared with the data derived from die 35.

When the scanning process reaches the right boundary of the care area of die 37, the stage is moved in the Y-direction an amount slightly less than the swath width and the stage starts a return trace in the X-direction. In this manner the care areas of the dice are traversed by the serpentine motion.

Die-to-database inspection, ordinarily performed on single die reticles, is similar to die-to-die inspection except that the comparison occurs between the die and a simulated image generated by database adaptor 18. FIG. 3 illustrates the die-to-database scan path 31'.

Review Operation

After completion of the automatic inspection operations, the operator reviews the defects by causing control computer 24 to move the stage 12 to the area of a particular defect and hold it there. The image is then scanned by acousto-optic scanners 40 and 42 in the Y-direction and by oscillating mirror 65 in the X-direction, and the digitized image is displayed on display 22. The operator may use the output of any of the detectors or the combination of outputs from more than one detector. If the operator desires, the different detector outputs may be superimposed and represented as separate colors on the display.

Phase Shift Material Thickness Measurement

Figure 10:
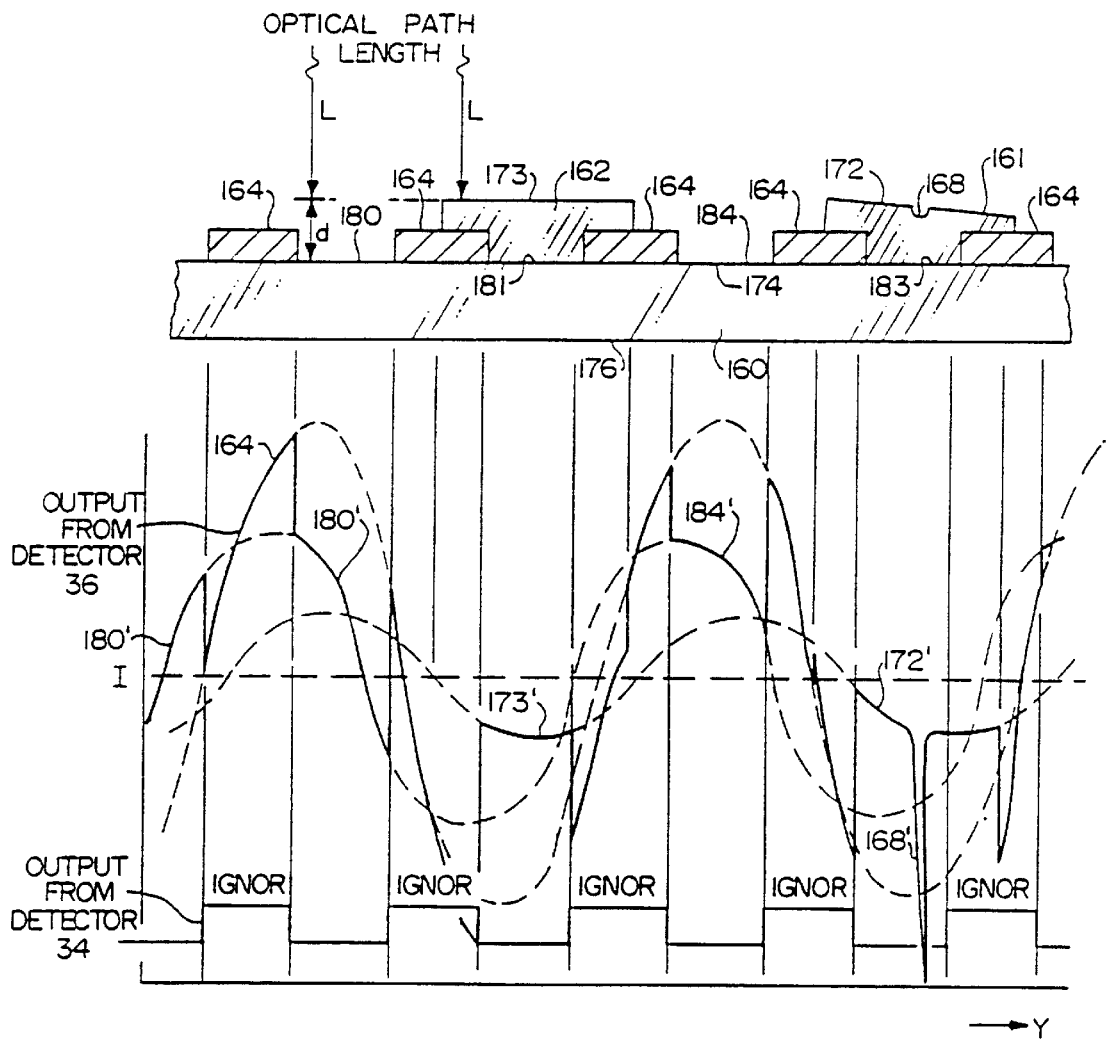
FIG. 10 is an illustration of a cross-section of a typical phase-shift mask showing in exaggerated scale an illustration of the phase-shifted output of the reflected beam detector.

FIG. 10 is an illustration of the cross section of one type of a phase shift mask. While the present example relates to a particular type of mask, on all types of masks, control of the thickness of phase shift material is a requirement and hence the technique described here is applicable to all types of phase shift masks.

The substrate 160 is typically of quartz on which opaque features 164 are deposited. These are typically thin layers of chrome. Phase shift features 161 and 162 made of transparent material will typically partially overlay part of the chrome 164 and some of the clear areas 181 and 183 between the features 164. Phase shift material filled transparent areas 181, 183 and clear areas 180, 184 typically alternate. The height of the upper surface 173 of the phase shift feature 162 above the level of the front, or upper, surface 174 of the quartz substrate is typically such that it produces a phase shift of 180 degrees with respect to a point 180 in the same plane but not covered by phase shift material.

Defects in phase shift masks may occur in several ways. There can be defects in the transparent areas, such as either excess chrome or dirt, or there can be missing chrome in a feature 164. Such defects are detected by the transmitted light detector 34 (FIG. 2) and are the subject of previously referenced prior art. The present invention is also capable of detecting defects in the phase shift layer 161 or 162. There are two types of defects: those where there is a sudden variation of thickness of the phase shift layer, and those in which there is a deviation from the desired thickness which is either constant, or varies slowly over the surface. The former type of defect, such as the divot 168 in layer 161, is detected by the transmitted light detector 34 because it scatters the light and hence does not allow the light to pass through the phase shift material. It therefore appears as a dark spot in transmission. Slowly varying surfaces 172 or incorrect thickness of the phase shift layer, such as depicted in feature 161, are detected by interferometric methods, as explained below.

Figure 11:
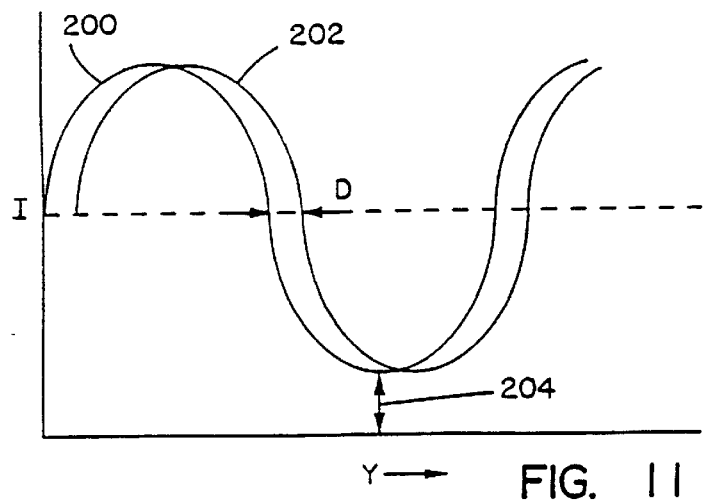
FIG. 11 is an illustration of the sinusoidally varying detected signal intensity as the mask is scanned in phase shift measurement mode.

A perfectly flat surface, such as 173 at the top of 162, parallel to the plane of the mask and with an optical path length L will produce fringes as the mask is scanned because, due to the tilted mirror 118, the wavefront of the reference beam is not parallel to the plane of the substrate. (In order to avoid any ambiguity in the direction of the change of the phase, the tilt of mirror 118 should be greater than the maximum expected slope of any surface such as 161.) The detector output in such a case is a sine wave, such as that shown in FIG. 11. A similar flat surface located at a path length L+D (see FIG. 10) will produce a sine wave of the same frequency but with a phase shift D with respect to curve 200. This second sine wave is shown as wave form 202.

As the mask is scanned in the Y-direction, the transmitted light detector 34 detects whether a particular pixel is fully transparent. Only at such fully transparent pixels are reflected light intensity measurements taken and digitized. At such pixels, the reflected light intensity is determined and digitized. This is suggested by the depiction at the bottom of FIG. 10 wherein it is indicated that during the time that the scan is passing across the non-transparent feature 164, as determined by the output of detector 34, the output of detector 36 is ignored. From the intensity value, and from the Y-coordinate of the pixel, together with the values of A, w and $I_o$ determined during the calibration, electronic subsystem 20 determines d in Equation 2 and the corresponding path length variation at the pixel, i.e., the height of the feature surface above plane 174.

It is to be noted that due to the periodic nature of a sinewave, there is an ambiguity because path length variations corresponding to a phase shift of 360 degrees are indistinguishable. However, sudden variations resulting in a 360° phase shift can occur only when the phase shift material contains a ridge. Such a ridge produces diffraction which is then detected in the transmission mode. Hence, the ambiguity due to a 360° phase shift is resolvable and it is possible to continuously, at every pixel, track the thickness of the phase shift material.

In practice, the mask substrates are not likely to be perfectly parallel to the image plane, nor is the substrate likely to be perfectly flat. However, these variations are gradual, and on a 5X phase shift mask one need consider variations only within a radius of 4–5 microns. Specifically, only the relative phase shift between two adjacent features is important, such as the relative phase shift between locations 180, 162 and 184. These points are likely to be less than 4 microns apart.

To determine whether there is a phase error of sufficient magnitude to indicate a defect on the substrate, the path length is computed at each transparent pixel covered by phase shift material 162 (FIG. 10). This value is then compared with the average of the path lengths of two adjacent points where there is no phase shift material, such as points 180 and 184. If the difference in path length differs from an acceptable value by more than a predetermined threshold value at the print wave length, such as 10 degrees for example, the phase shift material thickness at the inspected point is marked as defective.

In addition to making path length comparisons between points on geometric features in the same vicinity, the system also checks for a missing or extra geometric feature, such as may occur in the pattern generation. In die-to-die mode, the path lengths of pixels at 173, 180 and 184 (FIG. 10) of the 33 (FIG. 3) are compared with the path lengths at the corresponding pixels of die 35. This comparison will disclose any missing geometric features, unless both dice 33 and 35 have the same error. Similarly, in die-to-database mode a comparison can be made between the path lengths associated with the previously designated pixels and the description of these pixels in the CADs database.

Alternate Phase Shift Measurement Method

The above measurement technique uses a digital approach to determine the relative optical path length at grid points to determine the phase shift angle at every point. As explained below, one may also employ an analog method to find the phase shift angle.

Figure 12:
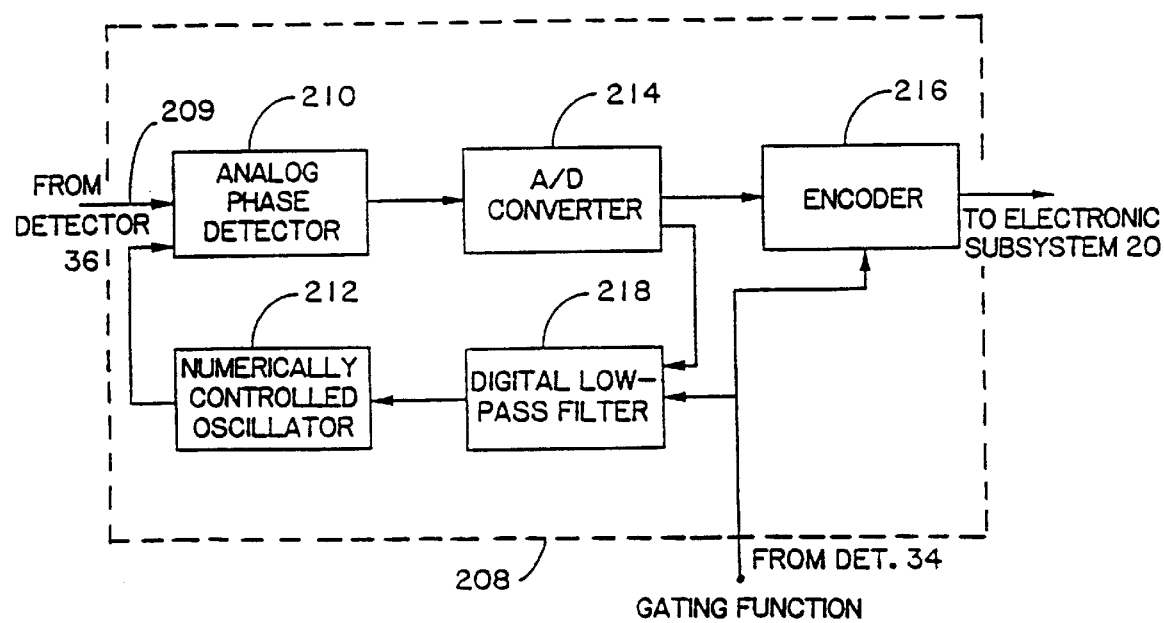
FIG. 12 is a block diagram depicting a phase-locked loop subsystem used to detect phase-shift material thickness.

FIG. 12 illustrates the additional circuitry required by this method for insertion into the apparatus of FIG. 1 at 208 to determine the phase shift angle. The analog signal derived from detector 36 is fed to one input 209 of an analog phase detector 210 which also obtains another signal at 211 from a numerically controlled oscillator 212. A signal proportional to the phase difference between these two signals is converted to a digital form by an eight bit A/D converter 214 and passed to an encoder 216 and also to a digital low pass filter 218. The digital filter 218 and the encoder 216 are gated by a gating signal derived from detector 34. The digital filter 218, which functions as an integrator, accepts an input only when detector 34 indicates that the mask is transparent at the inspected point. Encoder 216 accepts the 8-bit output signal of the A/D converter 214 and shifts it right one bit. If the pixel is transparent at that point, the encoder inserts a 0 into the most significant position of the digital signal and transmits the remaining signal to subsystem 20 as the phase signal. Should detector 34 indicate that the pixel is opaque, the digital signal will be encoded as all ones, 11111111. This signifies to the subsystem 20 that the phase signal is invalid and should be disregarded.

The previously explained circuitry is a phase-locked-loop that follows slow variations of the phase, as might be caused by slowly varying phenomena, such as imperfect flatness of the mask. The output of the encoder 216, when valid, indicates the path length variation in the local area.

Alternate Phase Shift Optical System Implementation

Figure 13A:
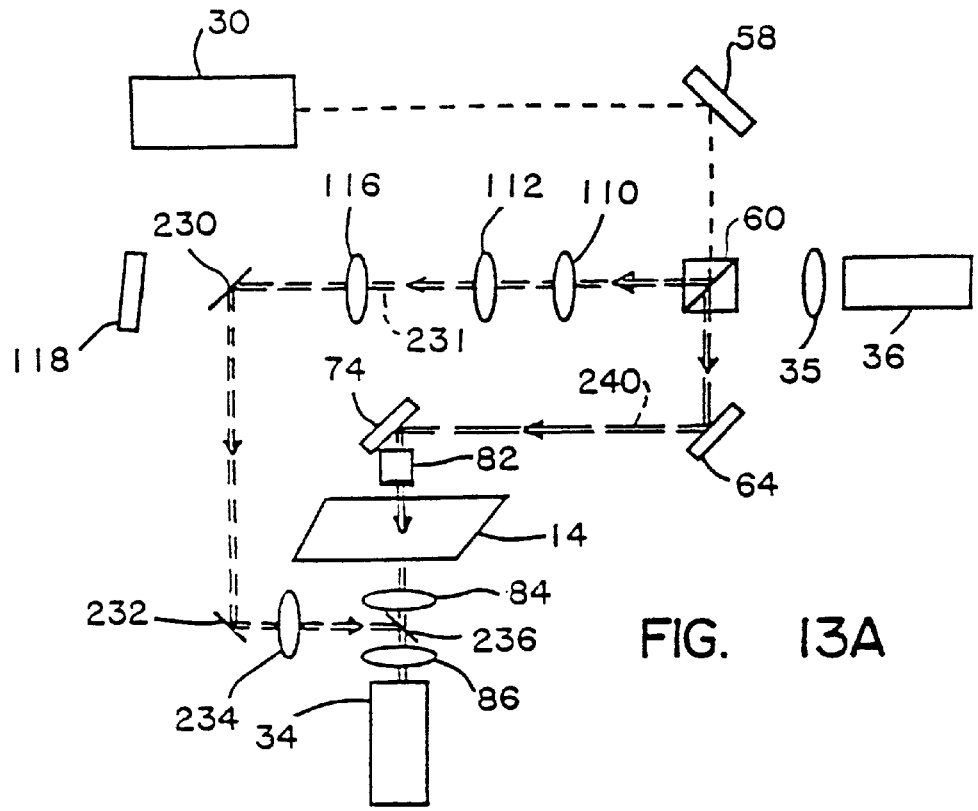
FIGS. 13a and 13b are simplified schematic diagrams respectively depicting operation of the optical subsystem used for measuring the phase-shift material thickness in the transmitted and reflected light modes.
Figure 13B:
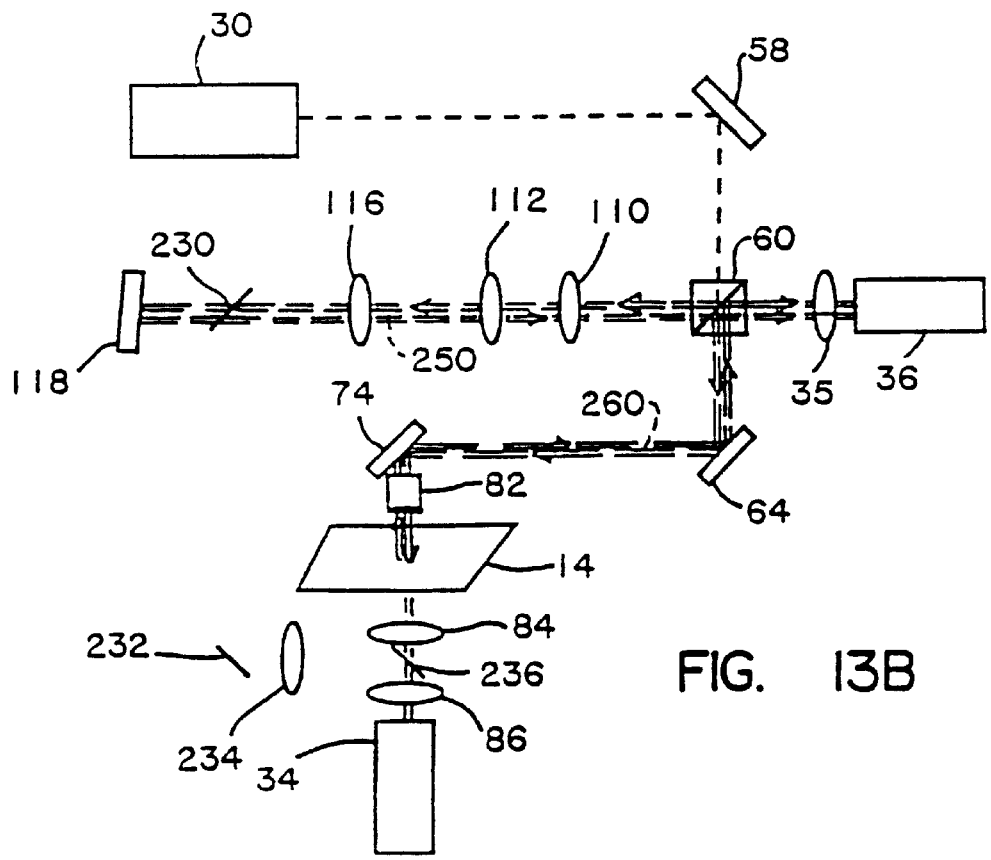

In some instances it is desirable to measure the actual phase shift, rather than infer the phase shift from the relative path length. This may be done by using transmitted interferometry. FIGS. 13a and 13b are simplified schematic diagrams, in which for simplicity many of the elements shown in FIG. 2 are omitted, but illustrate a variation of the preferred embodiment that permits measurement in either or both a transmit mode or a reflected mode using respectively transmitted light interferometry and simultaneous measurement of the reflected and transmitted interference pattern.

As depicted in FIG. 13a, to implement this alternative operating in the transmit mode, a pelicle beam splitter 230 is added which reflects light received from splitter 60 and produces a reference beam at detector 34 via the path 231 past tilted mirror 232, objective lens 234 and another beam splitter 236. The interference of the reference beam and the imaging beam passing along path 240 and through substrate 14 is detected at detector 34.

In the reflected light mode, reference light split by splitter 60 is directed along the path 250 to tilted mirror 118 and returned to detector 36 where it interferes with imaging light passing through splitter 60 and along the path 260 to substrate 20 where it is reflected back along path 260 and reflected by splitter 60 into detector 36.

It is to be noted that this alternative also permits the simultaneous measurement of the phase in both the reflected and transmitted modes.

Because lasers have a limited coherence length in both the reflected and transmitted interference modes, the path length should be approximately the same for the imaging beam path and the reference beam path.

Line Width Measurement

Figure 14:
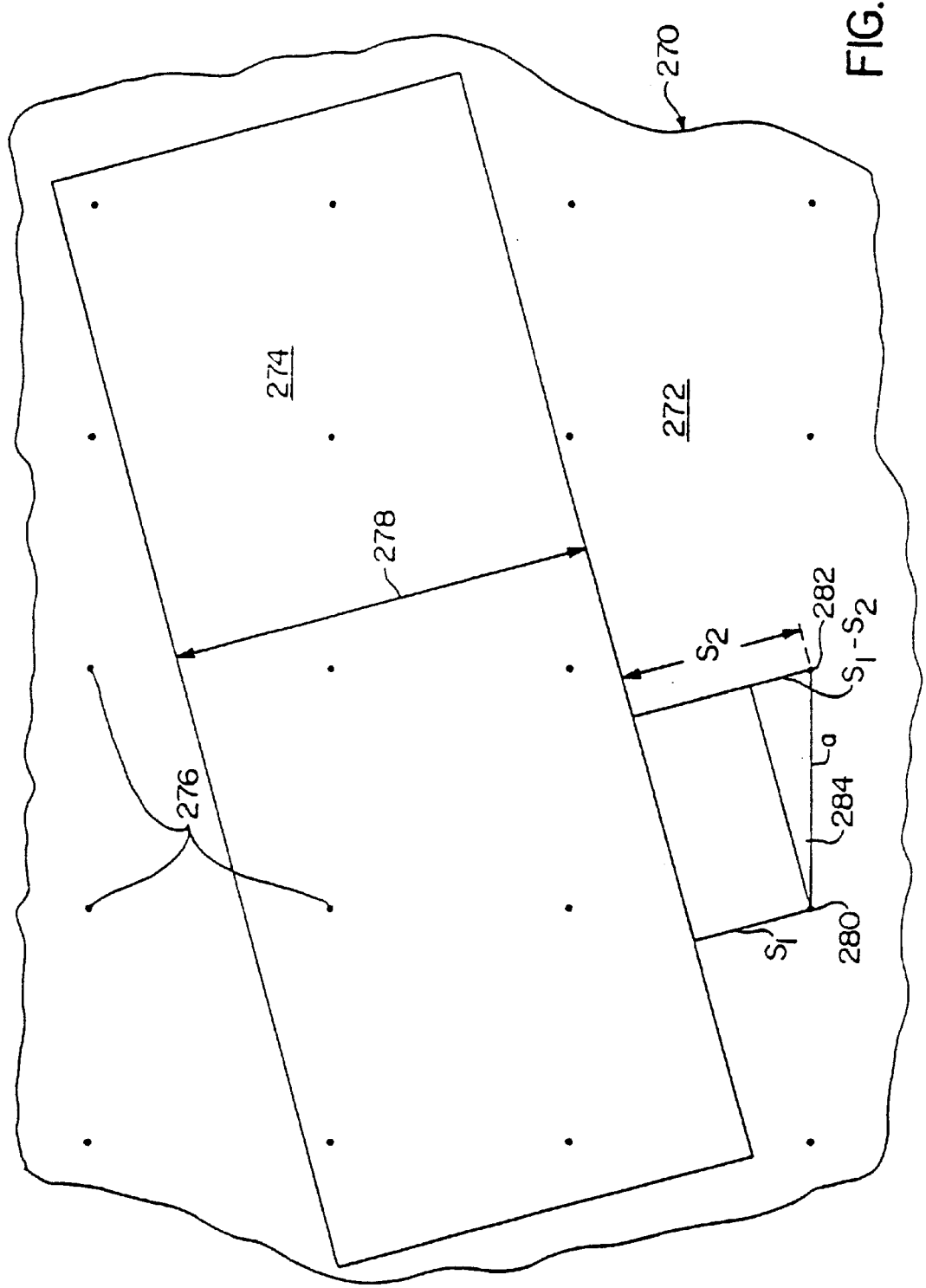
FIG. 14 is an illustration used to describe the method of linewidth measurement.

FIG. 14 shows a plan view of a small portion 270 of a mask. Area 272 is transparent and is crossed by a feature 274 that may either be opaque (chrome or other material) or transparent if the quartz substrate of the mask is covered by phase shift material. The system measures the intensity at equidistant grid points, depicted at 276. As explained more fully below, these intensity measurements are then used to determine the line width, i.e., the distance 278 across feature 274.

It is to be noted that at each of the grid points 276 the intensity is the convolution of the point spread function of the optical system with the transmissivity profile of the feature. Typically, the transmissivity profile is a step function. Therefore, for a straight feature, as is shown in FIG. 14, the intensity measured at a particular grid point is a function of the perpendicular distance from the grid point to the edge of the feature (line 274). The intensity at a particular point in the vicinity of a feature can thus be interpreted as the perpendicular distance from the point to the line. This interpretation is done in a simple table look-up operation in the computer 24 (FIG. 1). On the basis of the intensities at grid points 280 and 282, distances $S_1$ and $S_2$ are known and the slope of the edge relative to a feature is:

$$\tan G = \frac{S_2 - S_1}{(a^2 - (S_2 - S_1)^2)^{1/2}} \quad (4)$$

where a is the distance between the grid points 280 and 282 and G is angle 284.

Once the slope of the edge of a feature (line) has been determined, the opposite edge of the line can be similarly located, and a verification can be made that it is parallel to the previously calculated line edge. On the basis of the intensities along the two edges of the line, the linewidth is calculated in control computer 24.

The previously described method of line measurement is, strictly speaking, normally applicable only to conventional masks which have no surface areas covered by phase shift material. However, the technique described above may also be used for the measurement of phase shift features because, at the boundary between a clear area and an area covered by phase shift material, defraction of the incident light beam will occur and along this narrow boundary no light will be transmitted. The line width is the distance between the center of one boundary and the center of the opposite boundary.

Although the present invention has been described above in terms of preferred embodiments, it is anticipated that various alterations and modifications thereof will be apparent to those skilled in the art. For example, to avoid the need to sweep the laser beam during the scanning operation, instead of using the linear detector 34 in the preferred embodiment, one could use a time delay integrating sensor of the type described in the above-referenced Levy U.S. Pat. No. 4,579,455. With such modification, if a laser is used as the light source, coherence in the Y-direction would have to be destroyed by using a rotating ground glass. The coherence in the X-direction is destroyed by the time delay integrating sensor. It is therefore intended that the following claims be interpreted as covering all such alterations and modifications as fall within the true spirit and scope of the invention.

What is claimed is:

1. An optical inspection system for inspecting objects formed on substrates, comprising:

a stage for carrying a substrate to be inspected such that a surface of said substrate moves in at least two directions within an inspection plane;

laser means for providing an illuminating beam of light;

optical elements defining a first optical axis intersecting said inspection plane and along which said illuminating beam of light is initially passed, said optical elements including a variable magnification subsystem for focusing said beam of light to a spot on the substrate to be inspected;

a beam deflector disposed along said first optical axis and operative to deflect said beam of light in oscillatory fashion whereby said spot is caused to sweep across the surface of said substrate from one side to another of the path traced by the intersection of said optical axis with said substrate as said substrate is moved in said particular manner, and in a direction transverse to said path, as the substrate is carried along said path, the limits of deflection of said beam of light from one side of said path to the other defining the width of a scanning swath over a care area of the substrate including at least a portion of one of said objects;

a light detector for detecting changes in the intensity of said beam of light caused by its intersection with the inspected substrate as said beam of light is either transmitted or reflected by said substrate, said light detecting means being responsive to the detected changes in intensity and operative to develop scan signals corresponding thereby, said light detecting means including sampling means for sampling said scan signals to produce sample signals; and an electronic comparator for comparing said pixel sample signals to corresponding reference signals whereby differences therebetween are identified.

2. A method of inspecting objects formed on substrates, comprising the steps of:

transporting a substrate such that a surface thereof to be inspected moves within an inspection plane;

providing means defining a first optical axis intersecting said inspection plane;

directing a beam of light along said first optical axis and focusing said beam of light to illuminate a spot of a selected size on the substrate to be inspected;

sweeping said beam of light in oscillatory fashion such that the illuminated spot moves from one side to another of a path defined by the intersection of the optical axis with the substrate surface as said substrate surface is moved within said inspection plane whereby care areas of the substrate including at least one of said objects are scanned in swaths the width of which is determined by the beam sweep limits;

detecting changes in the intensity of said beam of light caused by its intersection with areas of the inspected substrate as said beam of light is either transmitted or reflected by said substrate, and developing scan signals corresponding thereto;

sampling said scan signals to produce sample signals; and comparing said sample signals to corresponding reference signals and identifying differences therebetween.

3. An optical inspection system for inspecting objects formed on substrates selected from the group consisting of photomasks, reticles, phase shift masks and semiconductor wafers including a plurality of supposedly identical patterned objects disposed in an ordered array on a surface thereof, comprising:

a laser for providing a pixel illuminating beam of light;

an optical system defining a first optical axis along which said pixel illuminating beam of light is to be initially passed;

a stage for moving a substrate to be inspected such that a surface thereof moves within an inspection plane intersected by said optical axis and such that as the substrate is moved the point of intersection traces a serpentine path over a portion of the substrate including at least one of the objects;

a beam deflector disposed along said first optical axis and operative to deflect said beam of light in oscillatory fashion such that said beam of light sweeps back and forth across said path from one side to another and in a direction generally transverse to said path such that, as the substrate is carried, the deflection of said beam of light from one side of said path to the other defines a scanning swath over the portion of the substrate;

a light detector for detecting changes in the intensity of said beam of light caused by pixel areas of the inspected substrate illuminated by said beam of light as said beam of light is either transmitted or reflected by said substrate, said light detector being responsive to the detected changes in intensity and operative to develop scan signals corresponding thereto;

an electronic circuit for storing first scan signals developed as said scanning swath passes over a first of the patterned objects and for comparing the stored first scan signals to second scan signals developed as the scanning swath passes over a second of the patterned objects whereby differences therebetween may be used to identify defects in the inspected substrate; and a recorder for recording the locations of said defects on said substrate.

4. An optical inspection system for inspecting objects formed on substrates selected from the group consisting of photomasks, reticles, phase shift masks and semiconductor wafers, comprising:

a stage for carrying a substrate to be inspected such that a surface of said substrate moves in a particular manner within an inspection plane;

a laser for providing a pixel illuminating beam of light;

an optical system defining a first optical axis intersecting said inspection plane and along which said pixel illuminating beam of light is initially passed, said optical system including a variable magnification subsystem for focusing said beam of light to a pixel defining spot on the substrate to be inspected;

a beam deflector disposed along said first optical axis and operative to deflect said beam of light in oscillatory fashion whereby said pixel defining spot is caused to sweep across the surface of said substrate from one side to another of the path traced by the intersection of said optical axis with said substrate as said substrate is moved in said particular manner, and in a direction transverse to said path, as the substrate is carried along said path, the limits of deflection of said beam of light from one side of said path to the other defining the width of a scanning swath over a care area of the substrate including at least a portion of one of said objects;

at least one light detector for detecting changes in the intensity of said beam of light caused by its intersection with the inspected substrate as said beam of light is either transmitted or reflected by said substrate, said light detector being responsive to the detected changes in intensity and operative to develop scan signals corresponding thereto, said light detector including a signal sample for sampling said scan signals to produce pixel sample signals; and an electronic comparator for comparing said pixel sample signals to corresponding reference signals whereby differences therebetween may be used to identify defects in the inspected substrate.

5. An optical inspection system for inspecting objects formed on substrates such as photomasks, reticles, phase shift masks and semiconductor wafers, comprising:

a stage for carrying a substrate to be inspected such that a surface of said substrate moves in a particular manner within an inspection plane;

a laser for providing a pixel illuminating beam of light;

an optical system defining a first optical axis intersecting said inspection plane and along which said pixel illuminating beam of light is initially passed, said optical system being operative to focus said beam of light to illuminate a pixel defining spot on the substrate to be inspected, the spot size determining at least one dimension of a pixel of the substrate;

a beam deflector disposed along said first optical axis and operative to deflect said beam of light in oscillatory fashion whereby said pixel defining spot is caused to sweep across the surface of said substrate from one side to another of a path traced by the intersection of said optical axis with said substrate as said substrate is moved in said particular manner, and in a direction transverse to said path as the substrate is carried along said path, the limits of deflection of said beam of light from one side of said path to the other defining the width of a scanning swath over care areas of the substrate including at least a portion of one of said objects;

at least one light detector for detecting changes in the intensity of said beam of light caused by its intersection with pixel areas of the inspected substrate as said beam of light is either transmitted or reflected by said substrate, said light detector being responsive to the detected changes in intensity and operative to develop scan signals corresponding thereto;

an electronic comparator for comparing said scan signals to corresponding reference signals whereby differences therebetween may be used to identify defects in the inspected substrate;

a recorder for recording the substrate locations of said defects;

a controller for subsequently causing said stage to reposition and hold the inspected substrate at a previously recorded location of a selected defect;

an oscillatory reflector disposed along said optical axis for causing a portion of said optical axis to sweep back and forth along a portion of said path in cooperation with said beam deflector whereby a selected segment of a swath is repetitively scanned and said light detector continuously generates display signals representative of the selected defect; and a display device responsive to said display signals and operative to provide a visual display of substrate area covered by the swath segment and including the selected defect.

6. An optical inspection system for inspecting objects formed on substrates selected from the group consisting of photomasks, reticles, phase shift masks and semiconductor wafers, comprising:

a laser for providing a pixel illuminating beam of light;

an optical system defining a first optical axis along which said pixel illuminating beam of light is to be passed;

a stage for moving a substrate to be inspected such that a surface thereof is carried within an inspection plane intersected by said optical axis and such that the point of intersection traces a serpentine path over at least a portion of the substrate including at least one of the objects to be inspected;

a beam deflector disposed along said first optical axis and operative to deflect said pixel illuminating beam of light in oscillatory fashion such that said beam of light sweeps back and forth across said path from one side to another and in a direction generally transverse to said path such that, as the substrate is carried, the deflection of said beam of light from one side of said path to the other defines a scanning swath over the portion of the substrate;

a light detector for detecting changes in the intensity of said beam of light caused by pixel areas of the inspected substrate illuminated by said beam of light as said beam of light is either transmitted or reflected by said substrate, said light detector being responsive to the detected changes in intensity and operative to develop scan signals corresponding thereto; and an electronic comparator for comparing said scan signals to corresponding reference signals whereby differences therebetween may be used to identify defects in the inspected substrate, and for recording the location of said defects on said substrate.

7. An optical inspection system as recited in claim 6 wherein said light detector includes a transmission detector disposed along said first optical axis on the side of said inspection plane opposite the side including said laser and operative to detect transmitted light passing through an inspected substrate, and wherein said optical system further includes defining a second optical axis along which said beam of light may be passed, said second optical axis not intersecting said inspected substrate but having at least a portion thereof in common with said first optical axis and intersecting said transmission detector whereby interferometric comparison between said beam of light and said transmitted light may be conducted.

8. An optical inspection system as recited in claim 6 wherein said stage is constrained to move within no more than two degrees of freedom, and is driven by x-direction and y-direction inputs generated by said electronic circuit.

9. An optical inspection system as recited in claim 8 wherein said stage is an X/Y air bearing stage driven by linear motors including stators and sliders separated by air bearings, the stators being configured to preload the air bearings of each slider in at least two directions.

10. An optical inspection system as recited in claim 6 wherein said laser is selected to have a predetermined wavelength of substantially the same wavelength as a light source to be later used in association with the inspected substrates during wafer processing.

11. An optical inspection system as recited in claim 6 wherein said optical system includes a rotator for rotating the direction of deflection of said beam of light so that it has a desired relationship to said predetermined path.

12. An optical inspection system as recited in claim 6 wherein said optical system also includes defining a second optical axis along which said beam of light may be passed, and having a portion thereof in common with a portion of said first optical axis, the optical path lengths of said first and second optical axes being substantially equal so that the two axes experience substantially identical thermal variation, said second optical axis including a tilted mirror for reflecting the beam of light back along said second optical axis and onto said light detector for interferometric comparison with light reflected back along said first optical axis from the substrate under inspection.

13. An optical inspection system as recited in claim 6 wherein said light-detector includes a first detector for detecting the intensity of light reflected from said substrate and for generating first scan signals commensurate therewith.

14. An optical inspection system as recited in claim 12 wherein said light detector further includes a second detector for detecting the intensity of light from said beam passing through the substrate under inspection and for generating second scan signals commensurate therewith.

15. An optical inspection system as recited in claim 14 wherein said electronic circuit compares said first and second scan signals to first and second reference signals and determines both the existence and type of any defect encountered.

16. An optical inspection system as recited in claim 6 wherein said light detector includes a transmitted light detector for detecting the intensity of light from said beam of light passing through the substrate under inspection and for generating corresponding scan signals.

17. An optical inspection system as recited in claim 6 wherein said light detector includes monitoring the intensity of said beam of light and generating an output which may be used by said electronic circuit to provide beam intensity variation correction to said scan signals.

18. An optical inspection system as recited in claim 6 wherein said beam deflector includes an acousto-optic modulator for causing said beam of light to be deflected back and forth over a relatively small angle, said angle being the factor which determines the width of said scanning swath.

19. An optical inspection system as recited in claim 6 and further comprising a database containing ideal data corresponding to the substrate under inspection, said data being selectively read out to generate said reference signals.

20. An optical inspection system as recited in claim 6 and further comprising storing said scan signals, the stored signals being subsequently used to provide said reference signals to which presently scanned signals may be compared.

21. An optical inspection system as recited in claim 6 wherein said light detector includes a first detector for detecting light transmitted through the substrate being inspected and a second detector for simultaneously detecting light reflected from the substrate being inspected, said first and second detectors respectively generating first and second signals from which said electronic circuit can determine both the existence of a defect and the type of defect detected.

22. An optical inspection system as recited in claim 6 and further comprising a second optical axis intersecting said first optical axis and operative to develop a beam of light for interfering with light reflected from the substrate under inspection to develop an interference beam for detection by said light detector such that the intensity of the interference beam detected by said light detector may be used by said electronic circuit to determine variations in the height of the inspected surface material above a particular surface of the inspected substrate.

23. An optical inspection system as recited in claim 6 and further comprising defining an auto-focus optical axis intersecting said first optical axis and including introducing astigmatism in the beam reflected from the surface of the inspected substrate, and an auto-focus detector for measuring the shape of the astigmatized beam and determining therefrom the degree of focus of the beam on the substrate, said auto-focus detector generating correction signals for input to said electronic circuit.

24. An optical inspection system as recited in claim 23 and further comprising a splitter for splitting said auto-focus optical axis into first and second branches having oppositely polarized anamorphous elements which distort the shape of the light beam passed therethrough, and wherein said auto-focus detector includes a first image shape detector associated with said first branch and a second image shape detector associated with said second branch, the outputs of said image shape detectors being used by said electronic circuit to determine whether said beam of light is in focus at said inspection plane, and if not in focus, to determine the degree and direction in which the beam is out of focus.

25. An optical inspection system as recited in claim 24 wherein said first and second image shape detectors are appropriately oriented quadrature detectors.

26. An optical inspection system as recited in claim 6 wherein said electronic circuit measures the magnitudes of said scan signals corresponding to predetermined grid points on the surface of the substrate under inspection and then uses such measurements to determine the surface dimensions of substrate features.

27. An optical inspection system as recited in claim 20 wherein said light detector includes a first detector for detecting the intensity of light reflected from the substrate under inspection and for generating first scan signals commensurate therewith.

28. An optical inspection system as recited in claim 27 wherein said light detector further includes a second detector for detecting the intensity of light from said beam passing through the substrate under inspection and for generating second scan signals commensurate therewith.

29. An optical inspection system as recited in claim 28 wherein said electronic circuit compares said first and second scan signals to corresponding first and second reference signals and determines both the existence and type of any defect encountered.

30. An optical inspection system as recited in claim 29 wherein said light detector includes a monitor for monitoring the intensity of said beam of light and generating an output which may be used by said electronic circuit to provide beam intensity variation correction to said scan signals.

31. An optical inspection system as recited in claim 30 and further comprising defining an auto-focus optical axis intersecting said first optical axis and including introducing astigmatism in the beam reflected from the surface of the inspected substrate, and an auto-focus detector for measuring the shape of the astigmatized beam and determining therefrom the degree of focus of the beam on the substrate, said auto-focus detector generating correction signals for input to said electronic circuit.

32. An optical inspection system as recited in claim 31 and further comprising a splitter for splitting said auto-focus optical axis into first and second branches having oppositely polarized anamorphous elements which distort the shape of the light beam passed therethrough, and wherein said auto-focus detector includes a first image shape detector associated with said first branch and a second image shape detector associated with said second branch, the outputs of said image shape detectors being used by said electronic circuit to determine whether said beam of light is in focus at said inspection plane, and if not in focus to determine the degree and direction in which the beam is out of focus.

33. An optical inspection system as recited in claim 32 wherein said first and second image shape detectors are appropriately oriented quadrature detectors.

34. An optical inspection system as recited in claim 33 wherein said electronic circuit measures the magnitude of said scan signals corresponding to predetermined grid points on the surface of the substrate under inspection and then uses such measurements to determine the surface dimensions of substrate features.

35. An optical inspection system as recited in claim 34 wherein said stage is an X/Y air bearing stage driven by linear motors including stators and sliders separated by air bearings, the stators being configured to preload the air bearings of each slider in at least two directions.

36. An optical inspection system as recited in claim 35 wherein said optical system includes a dove prism which may be used to rotate the direction of deflection of said beam of light so that it has a desired relationship to said predetermined path.

37. An optical inspection system as recited in claim 19 wherein said light detector includes a first detector for detecting the intensity of light reflected from said substrate and generating first scan signals commensurate therewith.

38. An optical inspection system as recited in claim 37 wherein said light detector further includes a second detector for detecting the intensity of light from said beam passing through the substrate under inspection and for generating second scan signals commensurate therewith.

39. An optical inspection system as recited in claim 38 wherein said electronic circuit compares said first and second scan signals to first and second reference signals and determines both the existence and type of any defect encountered.

40. An optical inspection system as recited in claim 39 and further comprising defining an auto-focus optical axis intersecting said first optical axis and including introducing astigmatism in the beam reflected from the surface of the inspected substrate, and an auto-focus detector for measuring the shape of the astigmatized beam and determining therefrom the degree of focus of the beam on the substrate, said auto-focus detector generating correction signals for input to said electronic circuit.

41. An optical inspection system as recited in claim 40 and further comprising a splitter for splitting said auto-focus optical axis into first and second branches having oppositely polarized anamorphous elements which distort the shape of the light beam passed therethrough, and wherein said auto-focus detector includes a first image shape detector associated with said first branch and a second image shape detector associated with said second branch, the outputs of said image shape detectors being used by said electronic circuit to determine whether said beam of light is in focus at said inspection plane, and if not in focus, to determine the degree and direction in which the beam is out of focus.

42. An optical inspection system as recited in claim 41 wherein said electronic circuit measures the magnitude of said scan signals corresponding to predetermined grid points on the surface of the substrate under inspection and then uses such measurements to determine the surface dimensions of substrate features.

43. An optical inspection system as recited in claim 42 wherein said stage is an X/Y air bearing stage driven by linear motors including stators and sliders separated by air bearings, the stators being configured to preload the air bearings of each slider in at least two directions.

44. An optical inspection system as recited in claim 7 wherein said optical system also includes defining a third optical axis along which said beam of light may be passed, and having a portion thereof in common with a portion of said first optical axis, the optical path lengths of said second and third optical axes being substantially equal so that the two axes experience substantially identical thermal variation, said third optical axis including a tilted mirror for spatially shifting and reflecting the spatially shifted beam of light back along said third optical axis and onto said reflection detector for interferometric comparison with light reflected along said first optical axis from the inspected substrate.

45. An optical inspection system as recited in claim 14 and further including a circuit responsive to said first and second scan signals and operative to develop gated signals for input to said electronic circuit to indicate defects in the inspected substrate as a function of the phase error between the light reflected from the surface of the substrate and the light passing through the inspected substrate.

46. An optical inspection system as recited in claim 45 wherein said circuit includes:

an analog phase detector for comparing said first scan signal to a reference signal to develop an analog signal proportional to the phase difference therebetween, a converter for converting said analog signal to a digital signal, and an encoder gated by said second scan signal and operative to generate said gated signals.

* * * * *